United States Patent [19]

Krause

[11] 3,965,171

[45] June 22, 1976

[54] PROCESS FOR THE PRODUCTION OF ETHER POLYCARBOXYLIC ACIDS

[75] Inventor: Horst-Jurgen Krause, Dusseldorf-Holthausen, Germany

[73] Assignee: Henkel & Cie G.m.b.H., Dusseldorf-Holthausen, Germany

[22] Filed: Sept. 25, 1975

[21] Appl. No.: 616,763

[30] Foreign Application Priority Data

Sept. 30, 1974  Germany............................ 2446686

[52] U.S. Cl. .................... 260/535 P; 260/448.2 B; 260/448.8 A; 260/484 P
[51] Int. Cl.² ........................................ C07C 59/22
[58] Field of Search................................ 260/535 P

[56] References Cited
UNITED STATES PATENTS 3,431,298  3/1969  Saotome et al.................. 260/535 P
3,870,749  3/1971  Danesh........................... 210/535 P

FOREIGN PATENTS OR APPLICATIONS 277,486  12/1930  Italy................................ 260/535 P

*Primary Examiner*—Paul J. Killos
*Attorney, Agent, or Firm*—Hammond & Littell

[57] ABSTRACT

A process for the production of ether polycarboxylic acids comprising reacting alkali metal salts of ether carboxylic acids with carbon dioxide in the presence of a silicon compound selected from the group of alkali metal alkoxy-silanolates and alkali metal alkoxy-polysiloxanolates and, optionally, inert diluents at temperatures of 200° to 350°C under pressure, acidify the resulting alkali metal salt of an ether polycarboxylic acid and recovering said ether polycarboxylic acid.

9 Claims, No Drawings

PROCESS FOR THE PRODUCTION OF ETHER POLYCARBOXYLIC ACIDS

THE PRIOR ART

It is known that ether polycarboxylic acids, as well as their alkali salts are good sequestering agents, particularly for the hardness-formers of water. But the practical use of these products was heretofore prevented by the fact that there was no economical production method for them. There is therefore a need for a method which permits the production of these compounds on a large technical scale.

U.S. Pat. No. 3,359,310 describes a method for the production of the potassium salt of malonic acid or malonic acid itself by the carboxylation of potassium acetate with carbon dioxide under pressure in the presence of potassium carbonate and a heavy metal catalyst at temperatures of about 300°C.

Furthermore, it was also known that metal salts of carboxylic acid can be substituted in the α-position with a metal, by reaction with an alkali metal, or an alkaline earth metal or their hydrides. This α-metalized carboxylic acid salt can then be subsequently carboxylated. However, one skilled in the art would not expect these reactions with their arduous conditions of pressure and temperature to be applied to labile ether carboxylic acids because, according to general knowledge, ethers are very easily cleaved by the action of metals at higher temperatures.

OBJECTS OF THE INVENTION

An object of the present invention is the development of a process for the production of ether polycarboxylic acids consisting of reacting an alkali metal salt selected from the group consisting of sodium and potassium of an ether carboxylic acid having the formula

wherein $R^1$ is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalykyl having 3 to 22 carbon atoms, polyoxaalkyl having 5 to 32 carbon atoms and 2 to 6 hetero oxygens, and carboxy substituted oxaalkyl having 3 to 22 carbon atoms and $R^2$ is a member selected from the group consisting of hydrogen and alkyl having from 1 to 4 carbon atoms with an excess of carbon dioxide in the presence of (1) at least an equimolar amount of a silicon compound selected from the group consisting of (a) an alkali metal alkoxy-silanolate having the formula

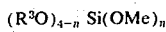

wherein $R^3$ is an alkyl having from 1 to 4 carbon atoms, Me is an alkali metal selected from the group consisting of sodium and potassium, and $n$ is an integer from 1 to 3 and (b) an alkali metal alkoxy-siloxanolate having the formula

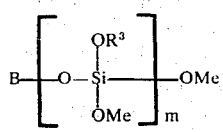

where Me and $R^3$ have the above assigned-values, B is selected from the group consisting of $R^3$ and Me and $m$ is an integer from 2 to 50, and (2) from 0 to 30% by weight, based on the weight of the reaction mixture of a finely-divided inert diluent, and an inert liquid diluent, at a temperature of between 200° and 350°C under a pressure of at least 2 atmospheres gauge, for a time sufficient to effect carboxylation, and recovering said ether polycarboxylic acids.

This and other objects of the invention will become more apparent as the description thereof proceeds.

DESCRIPTION OF THE INVENTION

The above objects were achieved and the problems of the prior art were overcome in that an ether carboxylic acid of the formula I

where $R^1$ denotes an alkyl with 1 to 22 carbon atoms, which can be straight-chain or branch-chain, and substituted by hydroxyl or carboxyl groups or interrupted by oxygen atoms, and where $R^2$ denotes hydrogen or a lower alkyl with 1 to 4 carbon atoms, is reacted in the form of its alkali metal salts selected from the group of sodium and potassium in the presence of a silicon compound selected from the group consisting of (a) an alkali metal alkoxy-silanolate having the formula II

wherein $R^3$ is an alkyl having from 1 to 4 carbon atoms, Me is an alkali metal selected from the group consisting of sodium and potassium, and $n$ is an integer from 1 to 3 and/or (b) an alkali metal alkoxy-siloxanolate having the formula III

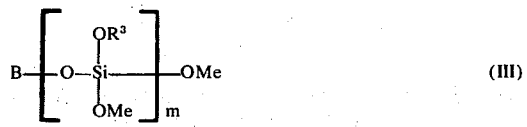

where Me and $R^3$ have the above assigned-value, B is selected from the group consisting of $R^3$ and Me and $m$ is an integer from 2 to 50, and optionally, inert diluents, with carbon dioxide at temperatures of 200° to 350°C, preferably 250° to 300°C, under pressure, and that the alkali metal salt of the ether polycarboxylic acids formed is transferred if necessary, in known manner into the free acids to give the desired ether polycarboxylic acids.

More particularly, the invention relates to a process for the production of ether polycarboxylic acids consisting of reacting an alkali metal salt of an acid carboxylic and having the formula

wherein $R^1$ is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and $R^2$ is a member selected from the group consisting of hydrogen and alkyl having from 1 to 4 carbon atoms with an excess of carbon dioxide in the presence of (1) at least an equimolar amount of a silicon compound selected from the group consisting of (a) an alkali metal alkoxy-silanolate having the formula

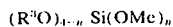

wherein $R^3$ is an alkyl having from 1 to 4 carbon atoms, Me is an alkali metal selected from the group consisting of sodium and potassium, and $n$ is an integer from 1 to 3 and (b) an alkali metal alkoxy-siloxanolate having the formula

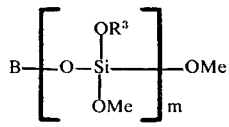

where Me and $R^3$ have the above assigned-values, B is selected from the group consisting of $R^3$ and Me and $m$ is an integer from 2 to 50, and (2) from 0 to 30% by weight, based on the weight of the reaction mixture of a finely-divided inert diluent, and an inert liquid diluent, at a temperature of between 200° and 350°C under pressure of at least 2 atmospheres gauge, for a time sufficient to effect carboxylation, and recovering said ether polycarboxylic acids.

As indicated above, U.S. Pat. No. 3,359,310 gives a process for the production of potassium malonate or malonic acid by carboxylation of potassium acetate with carbon dioxide under pressure in the presence of potassium carbonate and heavy metal catalysts at temperatures of about 300°C. Furthermore it was known that metal salts of carboxylic acids can be metallized in the α-position with alkali or alkaline earth metals or their hydrides and subsequently carboxylated. Application of these reactions with their adverse conditions of pressure and temperature to the labile ether carboxylic acids would seem out of the question for the man skilled in the art since, according to general knowledge, ethers are very easily split during metallization at higher temperatures.

It was completely unexpected, therefore, to find according to the invention that the alkali metal salts of the ethers of α-hydroxycarboxylic acids of the above-mentioned general formula II could be carboxylated with a high yield in the presence of alkali metal alkoxy-silanolates and/or alkali alkoxy-polysiloxanolates, and carbon dioxide under pressure, while maintaining certain temperature conditions. The carboxylation is effected on the carbon atom in the α-position to the carboxyl group. With ether carboxylic acids which contain several carboxyl groups in the molecule, carboxylation is possible on all carbon atoms which are in α-position to carboxyl groups or on only one carbon atom which is in the adjacent or α-position to a carboxyl group. The degree of reaction of the carboxylation depends to a great extent on the selected reaction conditions.

The carboxylation of the alkali metal salts of the ether carboxylic acids to be reacted takes place in the presence of alkali metal trialkoxy-silanolate according to the following reaction:

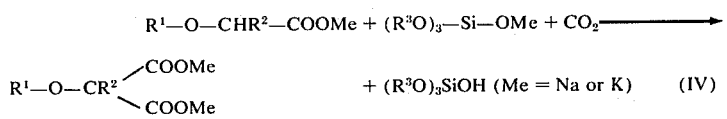

Where a dicarboxylic acid such as diglycolic acid is employed the reaction is as follows:

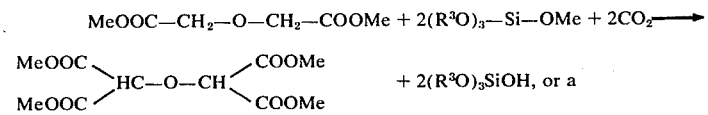

mixture of ether polycarboxylic acids are produced as follows:

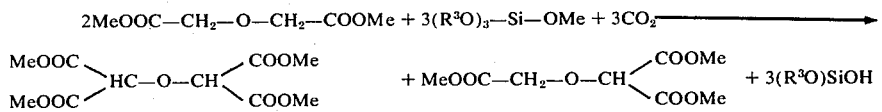

All alkali metal salts of ether carboxylic acids which meet the conditions of the above-mentioned general formula I can be used as starting materials for the production of the ether polycarboxylic acids according to the invention. Examples of such compounds suitable for carboxylation are the alkali metal salts of alkylglycolic acids such as methylglycolic acid, ethylglycolic acid, butylglycolic acid, laurylglycolic acid, Alkyl-$C_{12-18}$-glycolic acid, also oxaalklglycolic acids or polyoxaalkylglycolic acids such as etherification products of glycolic acids with ethylene-oxide (EO) addition products on alcohols, particularly on fatty alcohols, such as the lauryl alcohol + 2 EO ether of glycolic acid, myristic alcohol + 3 EO ether of glycolic acid, stearyl alcohol + 6 EO ether of glycolic acid; furthermore, carboxyl substituted alkylglycolic acids such as diglycolic acid, the lactic acid ether of glycolic acid, and carboxyl substituted oxaalkyl glycolic acids such as ethylene-bis-glycolic acid. Primarily, the potassium and sodium salts are employed as the alkali metal salts. The alkali metal salts of the ether carboxylic acids used as starting materials for the method according to the invention should be present if possible in dry form, since it is advisable to avoid the presence of large amounts of water during the reaction. Preferably, the reaction is conducted under substantially anhydrous conditions.

The production of the alkali metal salts of the ether carboxylic acids used as starting materials in the present method can be effected according to methods known from the literature, and is not the subject of the invention.

The alkali metal alkoxy-silanolates of the formula II can be obtained in analogy to the process described in Chemische Berichte, vol. 75 (1942), pages 530—531, by reacting tetraalkoxy-silanes whose alkyl groups contain 1 to 4 carbon atoms, such as tetramethoxy-silane, tetraethoxy-silane, tetra-i-propoxy-silane and tetra-n-butoxy-silane, with the corresponding amount of alkali metal hydroxide according to the reaction

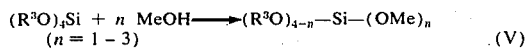

$$(R^3O)_4Si + n\ MeOH \longrightarrow (R^3O)_{4-n}-Si-(OMe)_n \qquad (V)$$
$$(n = 1 - 3)$$

Preferably a solution of an alkali metal hydroxide in methanol is used instead of the solid hydroxide. In the preparation of sodium alkoxy-silanotes, hydroxide solutions, are used with the advantage, which were obtained by mixing a methanolic sodium methylate solution with the calculated amount of water. The solid compounds of the formula II remain as a residue if methanol and the unreacted tetraalkoxy-silane is distilled off from the resulting reaction mixture. The products obtained this way correspond only approximately to the formulas to be expected from the selected molar ratio of alkali metal hydroxide to tetraalkoxy-silane, since the reaction can not be so guided that only one of the three possible alkali metal silanolates is formed in each case. The substances obtained always contain more alkali metal silanolate groups than corresponds to the respective reaction equation.

Disodium and dipotassium dialkoxy-silanoates can also be obtained according to a process known from German published application (DOS) No. 2,048,018 by heating the corresponding alkali metal trialkoxy-silanolates in the vacuum, with the tetraalkoxysilane formed under disproportionationing of the starting compound being continuously distilled off.

The alkali metal alkoxy-polysiloxanolates of the formula III are obtained by reacting alkali metal hydroxides with alkoxy-polysiloxanes, which in turn can be obtained by hydrolysis of the corresponding tetraalkoxy-silanes. The compounds of the formula III can also be contained as byproducts in the alkali metal alkoxysilanolates prepared according to reaction V, if the latter were not produced under anhydrous conditions.

In the reaction between the alkali metal salt of the ether carboxylic acid, carbon dioxide and alkoxysilanolate or alkoxy-polysiloxanolate, free silanols are formed whose OH groups react quickly with a $SiOR^3$ grouping with formation of a Si—O—Si bond, with the formation of $R^3OH$ alcohol. In order to obtain higher yields, it is advisable to remove the alcohol formed in the reaction continuously from the reaction mixture. This can be so effected, for example, in a reaction in the autoclave under carbon dioxide pressure, that the carbon dioxide pressure is relieved at certain intervals and the alcohol is constantly removed with the expanded carbon dioxide. For the complete removal of the alcohol formed, the vessel can be briefly evacuated, but naturally no air must get into the autoclave. Subsequently carbon dioxide is forced again into the autoclave with a compressor. But the reaction can also be carried out continuously under pressure with streaming carbon dioxide passed therethrough with constant removal of the alcohol formed. It is advisable to use a great excess of carbon dioxide to avoid secondary reactions.

The alkali metal salts of the ether carboxylic acids are reacted according to the invention with carbon dioxide under pressure in the presence of alkali metal alkoxy-silanolates and alkali metal alkoxy-polysiloxanolates. The pressure can vary within very wide limits. The desired reaction can already be obtained at a relatively low excess pressure, for example, at about 2 to 50 atm. gauge. In order to obtain good yields, it is generally adviseable, however, to apply a carbon dioxide pressure of more than 100 atm. gauge at the reaction temperature.

The upper limit of the pressure is determined by the available apparatus. It can be 1000 to 2000 atmospheres gauge or more. The pressure can be produced by corresponding pumps or compressors. In labortory tests, liquid or solid carbon dioxide can be filled into the cooled and evacuated reaction vessel. The carbon dioxide can be recirculated, just like the other ingredients.

The reaction temperature is very critical in the present method in order to avoid decomposition of the ether carboxylic acids. In order to obtain a sufficiently rapid reaction for technical purpose, temperatures above 200°C are required. The reaction temperature, however, should not exceed 350°C if possible, unless decomposition is prevented at the same time by very high pressures. A preferred temperature range is between 250° and 300°C. The optimum temperature depends on the desired degree of carboxylation as well as on the nature of the ether carboxylic acids used and the type of alkali metals used.

The reaction takes only a short time; but larger batches may take several hours, because of the required time for heating and cooling. Care must be taken that local overheating, which can lead to decomposition, is avoided during the heating step. For this reason, too rapid heating should be avoided. In general, a reaction time of 1 to 3 hours will be sufficient.

In carrying out the reaction as shown in reaction equation IV, it is necessary to employ, for each new carboxyl group to be formed, at least one equivalent alkali metal alkoxy-silanolate or alkali metal alkoxypolysiloxanolate which simultaneously neutralizes and stabilizes the newly formed carboxyl group during the metallization reaction. In some cases a slight excess of alkali metal silanolate is of advantage. The alkali metal alkoxy-silanolates and alkali metal alkoxy-polysiloxanolates are preferably used as finely divided powders. In some cases it may be advisable, in order to accelerate the start of the reaction, to add to the reaction charge a small amount of alcohol, preferably a lower alkanol such as methanol, or diethyl carbonate.

Preferably sodium trimethoxysilanolate, potassium trimethoxy-silanolate, disodium dimethoxy-silanolate and dipotassium dimethoxy-silanolate are employed as the silicon compound.

Water and oxygen should be excluded, as far as possible in the present method, as in all metalo-organic synthesis, if good yields are to be obtained. If necessary, water-binding substances can be added.

Furthermore, it was found advantageous to add to the reaction mixture, inert substances with a large surface area, such as kieselguhr, finely divided silica, powdered carbon black, finely divided aluminum oxide, in order to improve the mechanical-physical properties of the mixture and to prevent the possible formation of lumps. The technical realization of the method is thus made considerably easier. The amount of inert additives can vary within very wide limits and is determined by the design of the apparatus used. Ordinarily, from 0 to 20% by weight, based on the weight of the reaction mixture of the finely-divided inert diluents, are employed.

Finally, the reaction can also be carried out in the presence of inert liquid diluents, such as benzene, xylene, napthalene, diphenylene, diphenyl ether, or paraffin oil. The amount of diluent is preferably so selected that a pumpable mixture is obtained. Ordinarily, from 0 to 30% by weight, based on the weight of the reaction mixture, of the inert liquid diluents are employed.

The method can be carried out continuously or intermittently. Thus, for example, it is possible to work according to the fluidized bed method, or the turbulent flow continuous method. In an intermittent operation it is advisable to use rolling autoclaves or autoclaves equipped with a stirrer as the reaction vessels.

Thorough mixing of the reactants by stirring, shaking or grinding is also advisable in intermittent operations.

The reaction mixture can be worked up by dissolving the entire reaction mixture in water and filtering off the insoluble components, like the inert additives. The ether polycarboxylic acids formed can be obtained from the aqueous solution by acidification with mineral acids or by treatment with a cation exchanger in acid form and subsequent processing according to the known methods.

The ether polycarboxylic acids obtained can be used with very good results as sequestering agents. In many cases, particularly for use as sequestering agents for the hardness of the water in detergents and cleaning agents, it is not necessary to produce the ether carboxylic acids in the free acid form, their alkali metal salts can be used with just as good results. In addition, the product mixtures obtained in the method according to the invention can be used, after they have been separated from the inert substances.

The following examples will illustrate the invention without limiting it, however, to these examples.

EXAMPLES

In the following examples, the procedure was as follows, unless indicated otherwise. The dried anhydrous starting materials were finely ground in a ball mill and heated in a high-pressure autoclave of 500 ml capacity under carbon-dioxide pressure.

The "initial pressure" was the carbon dioxide pressure in the autoclave before commencing the heating. This pressure was adjusted in each case at 50°C, in view of the critical temperature of carbon dioxide. The "end pressure" was the maximum pressure observed at the corresponding reaction temperature.

For the working up of the reaction mixture, the crude product was dissolved in water and filtered hot. After cooling, the filtrate was mixed under stirring with a particulated cation exchange resin in acid form in order to acidify the product, whereby the carbon dioxide could escape without foaming. Subsequently the ion-exchange resin was filtered off and the aqueous solution of the ether polycarboxylic acids was conducted through a fresh cation exchange resin column in the acid form, in order to transfer it completely into the free acid. The eluate was evaporated under vacuum until dry. The total yield of the ether polycarboxylic acids obtained this way corresponds to the analytical composition of the reaction mixtures.

The analytical composition of the ether polycarboxylic acids obtained was determined by gas chromatography of the methyl esters after esterification of the acids with diazomethane. The usual analytical data were determined from the pure single fractions obtained by distillation or gas chromatography.

In the following tables of the following examples, the individual abbreviations have the following meanings:

init. pressure = the initial carbon dioxide pressure in atmospheres gauge measured at 50°C E-pressure = the maximum carbon dioxide pressure at the respective reaction temperature temp. = the reaction temp. in °C, measured in vapor area.

comp. TC% = the percent composition of total carboxylic acids

DG = diglycolic acid

CMT = carboxymethyl ether of tartronic acid (2-oxa-propane-1,1,3-tricarboxylic acid)

DT = ditartronic acid (2-Oxa-propane-1,1,3,3-tetracarboxylic acid)

MA + B = Malonic acid = byproducts

In the examples indentified by $x$, the alcohol formed was removed after a reaction time of 2 hours by releasing the pressure of the carbon dioxide. Subsequently a pressure of 150 atm. gauge was set at 240° to 260°C with fresh carbon dioxide and the reaction was completed in the course of an additional hour at the indicated temperature.

EXAMPLE 1

Preparation of the alkali metal alkoxy-silanolate

A solution of 27.0 gm (0.5 mol) of sodium methylate in methanol, prepared by reacting 11.5 gm (0.5 mol) of sodium with 200 ml of methanol, was first mixed with 9.0 gm (0.5 mol) of water, then with 76.1 gm (0.5 mol) of tetramethoxy-silane. The mixture was heated for about 15 minutes under reflux. Methanol and the unreacted tetramethoxy-silane were then distilled off under a water jet vacuum. Instead of the theoretically expected 80.1 gm (0.5 mol) of sodium trimethoxy-silanolate, only a residue of 66.0 gm solid product remained. The mixture thus consisted of sodium trimethoxy-siloanolate and oligosodium salts of oligomethoxy-silanolates.

Carboxylation of Diglycolic Acid

First 19.8 gm of this sodium methoxy-silanolate mixture (0.15 mol based on the silanolate groups) and then 21.0 gm (0.1 mol) of the dipotassium salt of diglycolic acid were dissolved in 200 ml methanol. After the methanol was distilled off, the residue was mixed with 4.0 gm finely divided silica (Aerosil 200; Degussa) obtained by flame hydrolysis, and ground in a ball mill.

The results of the reaction with carbon dioxide are contained in the following Table I.

Table 1

| Ex. | init. pressure | E-pressure | temp. °C | comp.TC% |
|---|---|---|---|---|
| 1$^x$ | 270/50°C | 870 | 270/2 h | 30.6 DG; 55.6CMT; |
| | 150/240°C | 270 | 270/1 h | 7.2DT; 6.6 MA + B |

EXAMPLE 2

Preparation of the alkali metal alkoxy-silanolate

A solution of 27.0 gm (0.5 mol) of sodium methylate in methanol, prepared by reacting 11.5 gm (0.5 mol) of sodium with 200 ml of methanol, was mixed first with 9.0 gm (0.5 mol) of water and then with 91.2 gm (0.7 mol) of tetramethoxy-silane. After the mixture had been heated for 15 minutes under reflux, methanol and unreacted tetramethoxysilane were distilled off under a water jet vacuum. 71.1 gm of a solid product remained as a residue. Since 80.1 gm (0.5 mol) of sodium trimethoxy-silanolate were expected theoretically, the product obtained represents a mixture of sodium trimethoxy-silanolate and sodium salts of oligomethoxy-silanolates.

Carboxylation of diglycolic acid 21.3 gm of this sodium methoxy-silanolate mixture (0.15 mol, based on the silanolate groups), 21.0 gm (0.1 mol) of the dipotassium salt of diglycolic acid and 4.0 gm of finely-divided silica were ground in a ball mill and subsequently reacted with carbon dioxide.

The results of the test are compiled in the following Table 2.

Table 2

| ex. | init. pressure | E-pressure | temp. °C | comp.TC% |
|---|---|---|---|---|
| 2 | 270/50°C | 810 | 270/3 h | 28.4DG; 48.1CMT 11.2DT; 12.3MA + B |

EXAMPLE 3

Preparation of the alkali metal alkoxy-silanolate

A solution of 91.2 gm (0.7 mol) of tetramethoxy-silane in 100 ml of methanol was mixed with a solution of 33.0 gm of 85% potassium hydroxide solution (0.5 mol KOH) in 200 ml of methanol. The mixture was heated for about 15 minutes under reflux. Subsequently methanol and excess tetramethoxy-silane were distilled off under a water jet vacuum. Instead of the theoretically expected 88.2 gm (0.5 mol) of potassium trimethoxysilanolate, 84.5 gm of solid potassium salts were obtained, that is, in addition to potassium trimethoxy-silanolate, also a small amount of oligopotassium oligomethoxy-silanolates were obtained.

Carboxylation of diglycolic acid 25.4 gm of this potassium methoxy-silanolate mixture (0.15 mol, based on the silanolate groups), 21.0 gm (0.1 mol) of the dipotassium salt of diglycolic acid and 4.0 gm of finely-divided silica were ground in a ball mill and subsequently reacted with carbon dioxide. The results of the test are contained in the following Table 3.

Table 3

| ex. | init. pressure | E-pressure | temp. °C | comp.TC% |
|---|---|---|---|---|
| 3 | 270/50°C | 825 | 270/2 h | 27.4DG;48.3GMT; |
|  | 150/250°C | 200 | 270/1 h | 11.8DT;12.5 MA + B |

EXAMPLE 4

Preparation of the alkali metal alkoxy-silanolate

A solution of 81 gm (1.5 mol) of sodium methylate in methanol, prepared by reacting 34.0 gm (1.5 mol) of sodium with 500 ml methanol, was mixed with 27.0 gm (1.5 mol) of water and subsequently with 1000 gm (6.6 mols) of tetramethoxy-silane. The mixture was heated for about 15 minutes under reflux. Then methanol and excess tetramethoxy-silane were distilled off under water jet-vacuum. 231.5 gm of sodium trimethoxy-silanolate were obtained. Theoretically 240.3 gm (1.5 mol) of this compound should have been formed.

100 gm of this sodium salt were heated for 10 hours to 180° to 210°C and the tetramethoxy-silane formed under disproportionationing was distilled off under a water jet vacuum. Instead of the theoretically expected 52.5 gm of disodium dimethoxy-silanolate, 54.1 gm of the product remained. The disodium salts obtained this way thus still contained a small amount of unreacted sodium trimethoxy-silanolate.

Carboxylation of diglycolic acid 25.2 gm (0.15 mol) of this disodium dimethoxy-silanolate, 21.0 gm (0.1 mol) of the dipotassium salt of diglycolic acid and 4.0 gm of finely-divided silica were ground in a ball mill and subsequently reacted with carbon dioxide.

The results of the test are contained in the following Table 4.

Table 4

| ex. | init. pressure | E-pressure | temp. °C | comp.TC% |
|---|---|---|---|---|
| 4 | 270/50°C | 850 | 270/2 h | 49.3DG; 37.5 CMT; |
|  | 150/255°C | 180 | 270/1 h | 2.5DT; 10.7B |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the production of ether polycarboxylic acids consisting of reacting an alkali metal salt selected from the group consisting of sodium and potassium of an ether carboxylic acid having the formula $$R^1 - O - CHR^2 - COOH$$

wherein $R^1$ is an member selected for the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and $R^2$ is a member selected from the group consisting of hydrogen and alkyl having from 1 to 4 carbon atoms with an excess of carbon dioxide in the presence of (1) at least an equimolar amount of a silicon compound selected form the group consisting of (a) an alkali metal alkoxy-silanolate having the formula $$(R^3O)_{4-n} Si (OMe)_n$$

wherein $R^3$ is an alkyl having from 1 to 4 carbon atoms, Me is an alkali metal selected from the group consisting of sodium and potassium, and $n$ is an integer from 1 to 3 and (b) an alkali metal alkoxy siloxanolate having the formula

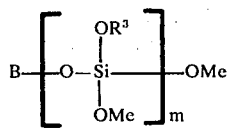

where Me and $R^3$ have the above assigned-values, B is selected from the group consisting of $R^3$ and Me and $m$ is an integer from 2 to 50, and (2) from o to 30% by weight, based on the weight of the reaction mixture of a finely-divided inert diluent, and an inert liquid diluent, at a temperature of between 200° and 350°C under a pressure of at least 2 atmospheres gauge, for a time sufficient to effect carboxylation, and recovering said ether polycarboxylic acids.

2. The method of claim 1 wherein said alkali metal salt of an ether carboxylic acid is the potassium salt.

3. The method of claim 1 wherein said alkali metal salt of an ether carboxylic acid is the sodium salt.

4. The method of claim 1 wherein said silicon compound is said alkali metal alkoxy-silanolate where $R^3$ is methyl and $n$ is an integer from 1 to 2.

5. The method of claim 1 wherein said silicon compound is sodium trimethoxy-silanolate.

6. The method of claim 1 wherein said silicon compound is disodium dimethoxy-silanolate.

7. The method of claim 1 wherein said reaction is conducted under substantially anhydrous conditions in the substantial absence of oxygen.

8. The method of claim 1 wherein up to 20% by weight of a finely-divided inert diluent is employed.

9. The method of claim 1 wherein R is carboxymethyl and $R^1$ is hydrogen.

* * * * *